(12) United States Patent
Condie et al.

(10) Patent No.: US 12,349,956 B2
(45) Date of Patent: Jul. 8, 2025

(54) CRYOABLATION ICEBALL FORMATION MONITORING DEVICES, SYSTEMS, AND METHODS

(71) Applicant: Boston Scientific Scimed Inc., Maple Grove, MN (US)

(72) Inventors: Catherine Condie, Shoreview, MN (US); Timothy A. Ostroot, Cokato, MN (US); Hong Cao, Maple Grove, MN (US); Andrew K. Zachman, St. Michael, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 609 days.

(21) Appl. No.: 17/752,612

(22) Filed: May 24, 2022

(65) Prior Publication Data
US 2022/0370114 A1    Nov. 24, 2022

Related U.S. Application Data

(60) Provisional application No. 63/192,470, filed on May 24, 2021.

(51) Int. Cl.
*A61B 18/02*      (2006.01)
*A61B 90/00*      (2016.01)
*A61B 18/00*      (2006.01)

(52) U.S. Cl.
CPC ............. *A61B 18/02* (2013.01); *A61B 90/37* (2016.02); *A61B 2018/00577* (2013.01); *A61B 2018/00875* (2013.01); *A61B 2018/0293* (2013.01)

(58) Field of Classification Search
CPC ..... A61B 18/02; A61B 18/1477; A61B 90/37; A61B 2018/00577; A61B 2018/00875;
(Continued)

(56) References Cited

U.S. PATENT DOCUMENTS

| 5,906,612 A | 5/1999 | Chinn |
| 6,190,378 B1 | 2/2001 | Jarvinen |

(Continued)

FOREIGN PATENT DOCUMENTS

| CN | 117355270 | 1/2024 |
| EP | 1223875 | 12/2004 |

(Continued)

OTHER PUBLICATIONS

"Examination Report," for Australian Patent Application No. 2022280013 mailed Jun. 11, 2024 (3 pages).

(Continued)

*Primary Examiner* — Ankit D Tejani
*Assistant Examiner* — Joshua Brendon Solomon
(74) *Attorney, Agent, or Firm* — Pauly, DeVries Smith & Deffner LLC

(57) ABSTRACT

Disclosed herein are devices, systems, and methods for monitoring a formation of an iceball at a cryoablation needle. An example method includes receiving an impedance from at least one electrode in an electrode arrangement that is disposed at a cryoablation needle distal portion. The electrode arrangement is configured to engage the iceball as the iceball is formed over the cryoablation needle distal portion so as to cause a change in the impedance. The example method includes determining one or more physical attributes of the iceball based on a rate of the change in the impedance.

20 Claims, 8 Drawing Sheets

(58) Field of Classification Search
CPC .... A61B 2018/0293; A61B 2018/0212; A61B 2018/0262; A61B 2090/061; A61B 2562/227

See application file for complete search history.

(56) References Cited

U.S. PATENT DOCUMENTS

| | | |
|---|---|---|
| 2005/0177146 A1 | 8/2005 | Sherman |
| 2014/0088578 A1 | 3/2014 | Rubinsky et al. |
| 2019/0142494 A1* | 5/2019 | Cross ............. A61B 18/0206 607/2 |
| 2022/0370114 A1 | 11/2022 | Condie et al. |

FOREIGN PATENT DOCUMENTS

| | | |
|---|---|---|
| JP | 2024515877 | 4/2024 |
| WO | 2017009165 | 1/2017 |

OTHER PUBLICATIONS

"International Preliminary Report on Patentability," for PCT Application No. PCT/US2022/030754 mailed Nov. 21, 2023 (10 pages).

"International Search Report," for PCT Application No. PCT/US2022/030754 mailed Sep. 9, 2022 (6 pages).

"Office Action," for Japanese Patent Application No. 2023-566854 mailed Oct. 8, 2024 (13 pages) with English translation.

"Response to Examination Report," for Australian Patent Application No. 2022280013 filed Sep. 26, 2024 (16 pages).

"Response to Office Action," for Japanese Patent Application No. 2023-566854 filed Nov. 29, 2024 (6 pages) no English translation.

Hartov, Alex, et al., "Using multiple-electrode impedance measurements to monitor cryosurgery," Medical Physics, AIP, Melville, NY, US, vol. 29, No. 12, Dec. 1, 2002 (Dec. 1, 2002), pp. 2806-2814, XP012011683, ISSN: 0094-2405, DOI: 10.1118/1.1521721 (abstract only)., 2806-2814.

"Decision of Rejection," for Japanese Patent Application No. 2023-566854 mailed Mar. 11, 2025 (8 pages) with English translation.

* cited by examiner

CRYOABLATION ICEBALL FORMATION MONITORING DEVICES, SYSTEMS, AND METHODS

CROSS REFERENCE TO RELATED APPLICATIONS

This application claims priority to Provisional Application No. 63/192,470, filed May 24, 2021, which is herein incorporated by reference in its entirety.

TECHNICAL FIELD

The present invention pertains generally to the field of cryosurgery. More particularly, the present invention pertains to cryoablation needless for use on tumors or other tissues.

BACKGROUND

Cryosurgical systems comprise one or more cryoablation needles connected to one or more cryogen sources. One common use for these systems is the ablation of tumors or tissue by subjecting them to freeze thaw cycles. In such systems, the cryogen is delivered from the cryogen source to the cryoablation needles, where expansion of the cryogen (e.g., cryogen liquids such as liquid nitrogen and/or cryogen gases such as nitrogen, nitrous oxide, oxygen, argon, etc.) leads to rapid cooling of the needle tip, thereby freezing tissue in the vicinity of the needle tip. In one type of cryoablation procedure, the physician places metal (e.g., stainless steel) probes percutaneously into the patient's body under ultrasound guidance. Cryogen is then circulated through the probes, creating an expanding layer of ice (e.g., an "iceball") throughout the tumor and/or tissue. This process can be monitored by using conventional medical imaging (e.g., computed tomography (or "CT"), transcutaneous-ultrasonography (TUS), or MRI imaging depending on the application) to watch as freezing progresses within the tumor or tissue. The cycle of freezing and thawing of tissue results in coagulation necrosis of the tissue.

While somewhat useful, conventional monitoring methods present several downfalls. During cryoablation of tumors and/or other tissue using such cryosurgical systems, the clinician monitors the ice formation closely for several reasons. For example, such monitoring can be useful to verify that the ice adequately covers the tissue and/or tumor with margin. In another example, such monitoring can be useful to protect critical structures from the cryoablation. CT, ultrasound, or MRI imaging methods are not conducive to real time monitoring. They provide a snapshot in time. In addition, frequent CT images subject the patient to excessive radiation. In some tissue (for example bone and lung), it is difficult to see the iceball. MRI imaging can cause excessive heating on the needle shaft.

SUMMARY

In Example 1, a method includes receiving an impedance from at least one electrode in an electrode arrangement that is disposed at a cryoablation needle distal portion. The electrode arrangement is configured to engage the iceball as the iceball is formed over the cryoablation needle distal portion so as to cause a change in the impedance. The example method includes determining one or more physical attributes of the iceball based on a rate of the change in the impedance.

According to another example further to Example 1 ("Example 2"), the method can include the one or more physical attributes includes at least one of a size and a shape of the iceball and, optionally, wherein the rate of the change in the impedance is based on at least one reference location that is positioned at the cryoablation needle.

According to another example further to Example 2 ("Example 3"), the at least one reference location includes a first reference location that is positioned a distance from a tip section of the cryoablation needle distal portion to the at least one electrode.

According to another example further to Example 2 ("Example 4"), the electrode arrangement comprises a plurality of electrodes such that the at least one electrode is a first electrode and such that the plurality of electrodes includes the first electrode and a second electrode, wherein the at least one reference location defines a distance that is indicative of a distance between the first electrode and the second electrode and, optionally, wherein the second electrode is disposed at a position that is proximal to the first electrode.

According to another example further to Examples 1-4 ("Example 5"), the cryoablation needle comprises a needle body that is formed of a conducive material and a sheath that is configured to receive the needle body so as to form one or more exposed regions of the needle body and one or more unexposed regions of the needle body, wherein the at least one electrode comprises a first exposed region of the one or more exposed regions.

According to another example further to Example 5 ("Example 6"), the at least one electrode comprises a plurality of electrodes and the one or more exposed regions comprises a plurality of exposed regions such that each of the electrodes in the plurality of electrodes corresponds to an exposed region within the plurality of exposed regions or wherein the needle body is movably received with the sheath.

According to another example further to Examples 1-6 ("Example 7"), determining one or more physical attributes of the iceball based on the rate of the change in the impedance comprises using a transfer function that correlates the one or more physical attributes to the rate of the change in the impedance and, optionally, wherein determining the one or more physical attributes of the iceball based on the rate of the change in the impedance is performed via a processor that is in communication with the electrode arrangement.

In Example 8, a non-transitory computer-readable medium having processor-executable instructions for reading data from a processor in communication with at least one electrode in an electrode arrangement disposed at a cryoablation needle, the processor-executable instructions when installed on a device enable the device to perform actions comprising receiving an impedance from the at least one electrode in the electrode arrangement that is disposed at a cryoablation needle distal portion, the electrode arrangement is configured to engage an iceball as the iceball is formed over the cryoablation needle distal portion so as to cause a change in the impedance and determining one or more physical attributes of the iceball based on at least one of the impedance and a reference location that is positioned at the cryoablation needle.

According to another example further to Example 8 ("Example 9"), the one or more physical attributes includes at least one of a size and a shape of the iceball.

According to another example further to Examples 8-9 ("Example 10"), the actions further comprise generating, via a display device, an illustration of an iceball that has the one or more physical attributes that have been determined; monitoring a formation of the iceball; and updating the illustration of the iceball when the one or more physical attributes of the iceball changes.

According to another example further to Examples 8-10 ("Example 11"), determining a physical attribute of the iceball based on at least one of the impedance and the reference location that is positioned at the cryoablation needle comprises using a transfer function that correlates the physical attribute to a rate of the change in the impedance.

According to another example further to Examples 8-11 ("Example 12"), the actions further comprise determining whether one or more iceballs have coalesced.

In Example 13, a cryoablation needle comprising a needle body that has a proximal portion and a distal portion that is opposite the proximal portion; an electrode arrangement that includes at least one electrode; the electrode arrangement disposed at the distal portion of the cryoablation needle, the at least one electrode configured to generate an impedance; and a conductor wire assembly that includes at least one conductor wire, the conductor wire assembly is in communication with the electrode arrangement such that measures that are indicative of a size or a shape of the iceball can be determined based a rate of change in the impedance.

According to another example further to Example 13 ("Example 14"), the cryoablation needle comprises a needle body that is formed of a conducive material and a sheath that is configured to receive the needle body so as to form one or more exposed regions of the needle body and one or more unexposed regions of the needle body, wherein the at least one electrode comprises a first exposed region of the one or more exposed regions, wherein the at least one electrode comprises a plurality of electrodes and the one or more exposed regions comprises a plurality of exposed regions such that each of the electrodes in the plurality of electrodes corresponds to an exposed region within the plurality of exposed regions, and, optionally, wherein the needle body is movably received with the sheath.

According to another example further to Examples 13-14 ("Example 15") the electrode arrangement comprises a plurality of electrodes such that the at least one electrode is a first electrode and such that the plurality of electrodes includes the first electrode and a second electrode; and wherein the rate of change in the impedance is based on at least one reference location that is indicative of a distance from a tip section of a cryoablation needle distal portion to either the first electrode or the second electrode or a distance that corresponds to the distance between the first electrode and the second electrode.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
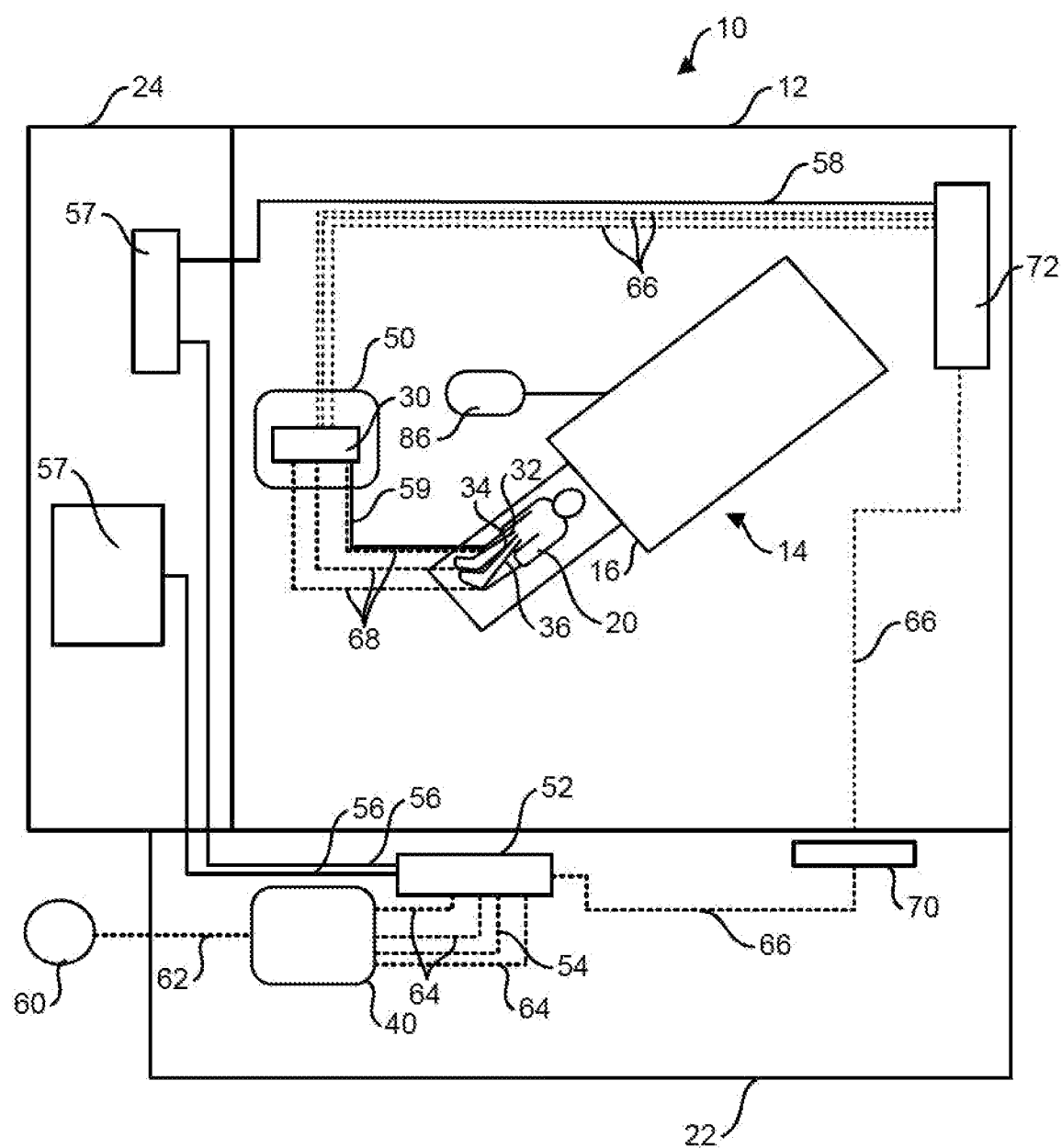
FIG. 1 is a schematic representation of a cryosurgery environment.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

For the purposes of promoting an understanding of the principles of the present disclosure, reference is now made to the examples illustrated in the drawings, which are described below. The exemplary examples disclosed herein are not intended to be exhaustive or to limit the disclosure to the precise form disclosed in the following detailed description. Rather, these exemplary examples were chosen and described so that others skilled in the art can utilize their teachings. It is not beyond the scope of this disclosure to have a number (e.g., all) the features in a given example to be used across all examples.

Disclosed herein are principles that can be employed in cryosurgical systems to inform a physician of information related to iceball formation. FIG. 1 shows a schematic representation of a cryosurgery environment. In particular, FIG. 1 is a schematic of a Magnetic Resonance Imaging (hereinafter "MRI")-guided cryosurgery system 10 according to non-limiting examples of the present disclosure.

Cryosurgical systems can be used for cryoablating target tissues (e.g, tissue and/or a tumor). Typically, such systems include one or more cryoablation needles, one or more cryogen sources 60 and a controller. The cryogen sources 60 can supply gases (e.g., cryogases) such as argon, nitrogen, air, krypton, $CO_2$, CF4, xenon, and various other gases. As used herein, "cryogen" can refer to any fluid or gas that reaches low temperatures (e.g., below 170 Kelvin). In some non-limiting examples, the fluid can reach low temperatures (e.g., below 170 Kelvin) when pressurized to pressures greater than about 1000 psi (e.g., typically around 3500 psi) and permitted to undergo expansion (e.g., Joule-Thomson expansion as further discussed below). The cryosurgical system 10 can also include a controller having one or more sensors, flow meters, timers, analog/digital converters, wired or wireless communication modules, etc. In addition, the controller can regulate one or more of flow rates, temperatures, and pressures of cryogen supplied to the cryoablation needle 100. media During cryosurgery, for instance, a surgeon may deploy one or more cryoablation needles within a patient 20. These cryoablation needles can cryoablate a target area of a patient anatomy by placing the cryoablation needle 100 at or near the target area of the patient anatomy. In an example, the cryoablation needle 100 uses the Joule-Thomson effect to produce cooling or heating. In such cases, a cryogen expands in the cryoablation needle 100 from a higher pressure to a lower pressure. Expansion of the cryogen results in temperatures at or below those necessary for cryoablating a tissue in the vicinity of the tip of the cryoablation needle 100. Heat transfer between the expanded cryogen and the outer walls of the cryoablation needle 100 can be used to form an iceball, and consequently cryoablate the tissue.

The system 10 of FIG. 1 can include a magnet room 12 comprising an MRI scanner 14 comprising an MRI magnet 16 for accommodating a patient 20. The MRI magnet 16 can be of an open or closed type and can include access ports to allow a surgeon to access the patient 20. The MRI magnet 16 can also have electrical connection lines (illustrated by solid lines) and/or mechanical connection lines (illustrated by dashed lines) in FIG. 1 for connecting to various electrical, control and/or cryoablation systems as will be described further below. The system 10 can include a control room 22 electrically (and/or magnetically) isolated from the magnet room 12 (by electrical and/or magnetic isolation 23), and an equipment room 24. The MRI system 10 may be used to image the patient 20 before insertion of surgical tools 32 to visualize patient 20 areas of interest, such as a tumor or a patient 20 cavity. Further, imaging may be performed during insertion to guide the surgical tool to the intended location inside the patient 20. Additionally, imaging may be performed after insertion and during surgery, as well as after surgery.

Continuing with FIG. 1, in a non-limiting example, the connection lines may terminate in one or more surgical tools 32, such as cryoablation needles insertable inside a patient 20. Accordingly, in some such examples, the system 10 may include a connector interface 30 placed inside the magnet room 12 to permit connection of one or more surgical tools 32, 34, 36 to other components of the cryoablation systems that may be placed outside the magnet room 12 (for instance, in a control room 22 or an equipment room 24). For instance, the system 10 may include electrical connection lines and fluid connection lines extending from the control room 22 to the magnet room 12, so as to operatively connect a control system 40 to the surgical tools 32. The connector interface 30 can, in some examples, be provided on a cart 50 (which may be stationary or mobile) positioned proximal to the magnet to permit a plurality of surgical tools 32 to be directly or indirectly (e.g., electrically and/or fluidly) connected to the control system 40 positioned outside the magnet room 12 (e.g., in the control room 22). In the illustrated embodiment, the cart 50 is a mobile cart 50.

The electrical and fluid connections between the control system 40 and the surgical tools 32 will be described according to an example. The control system 40 can be electrically connected to a junction box 52 located external to the magnet room 12 by way of a first set of electrical connection lines 54. Further, the junction box 52 can include a second set of electrical connection lines 56 to connect to electrical and/or imaging equipment 57 (such as an imaging router and electrical filters) located external to the magnet room 12 (for instance, within the equipment room 24). A third set of electrical connection lines 58 may connect the electrical and/or imaging equipment 57 to the connector interface 30 and/or mobile cart 50 located inside the magnet room 12. The junction box 52 can permit removable electrical connection between components in the magnet room 12 and components in the electrical and/or control rooms.

Referring again to FIG. 1, in some examples, the system 10 may be used to perform cryosurgical procedures (e.g., cryoablation). Accordingly, in some examples, the system 10 may include one or more cryogen sources 60. The cryogen source can be a liquid or gas container that can provide a fluid at cryogenic temperatures and pressures to surgical tools 32 (e.g., cryoablation needles). The cryogen source can be a cooling gas such as argon, nitrogen, air, krypton, $CF_4$ xenon, or N2O.

As can be seen from FIG. 1, the cryogen source is positioned outside the magnet room 12 and is fluidly connectable to the control system 40 by way of a first set of fluid connection lines 62. The control system 40 in turn can be fluidly connected to the connector interface 30 and/or mobile cart 50 by way of a second set of fluid connection lines 64 and a third set of fluid connection lines 66. A fourth set of fluid connection lines 68 can fluidly connect the surgical tools 32 (e.g., cryoablation needles) to the connector interface 30 and/or mobile cart 50. The fluid lines can be flexible and/or detachable and may include other fluid components to regulate pressure of fluid passing therethrough. Fluid from the cryogen source may thus be conveyed by the set of fluid connection lines 62, 64, 66 and 68 to the surgical tools 32. Optionally, the system 10 can include a fluid connection panel 70 electrically isolated from the magnet room 12 so as to permit fluid connections between components present in the magnet room 12 and those in the control room 22. Similarly, an electrical connection panel 72 can facilitate electrical connections between components present in the magnet room 12 and those in the control room 22 and/or electrical room.

Turning toward discussion about certain exemplary features of the present disclosure, as an initial matter, several advantages are provided by employing the principles disclosed herein. For instance, in an example of many examples disclosed herein, principles of the present disclosure include measuring AC electrical impedances (e.g., in the range from 1 kHz to 1 MHz) to identify iceball formation on cryoablation needles. This formation includes physical attributes of the iceball relative to the cryoablation needle such as iceball diameter, iceball length along the cryoablation needle, and coalescence of iceballs between two or more needles. Such principles can be advantageous over existing monitoring methods and imaging modalities (e.g., MRI, ultrasound, or CT). Among these advantages are the ability to provide continuous monitoring without need for physician engagement, a reduction in radiation exposure (e.g., from CT) for the patient, and monitoring iceball formation where current imaging modalities do not work well, such as in bone and in the spinal cord. Below, these principles and advantages of the present disclosure are further discussed in detail with reference to the figures and/or will be apparent to one skilled in the art armed with this disclosure.

Discussion of various examples according to principles of the present disclosure are discussed in further detail below. For instance, the discussion begins with an example of a single-electrode cryoablation needle followed by discussions about an example of a multiple-electrode cryoablation needle and a sheathed cryoablation needle respectively. These are just some examples of the many examples contemplated by this disclosure. As such, as noted throughout the below discussion, no limitations on this disclosure should be drawn by the discussion of these examples. As well, it is contemplated that any features across these examples can be combined in whole or in part without departing from the scope of this disclosure. Further, one skilled in the art will appreciate that other variations logically extend from those discussed herein. Those too should not be considered outside the scope of this disclosure.

Figure 2A:
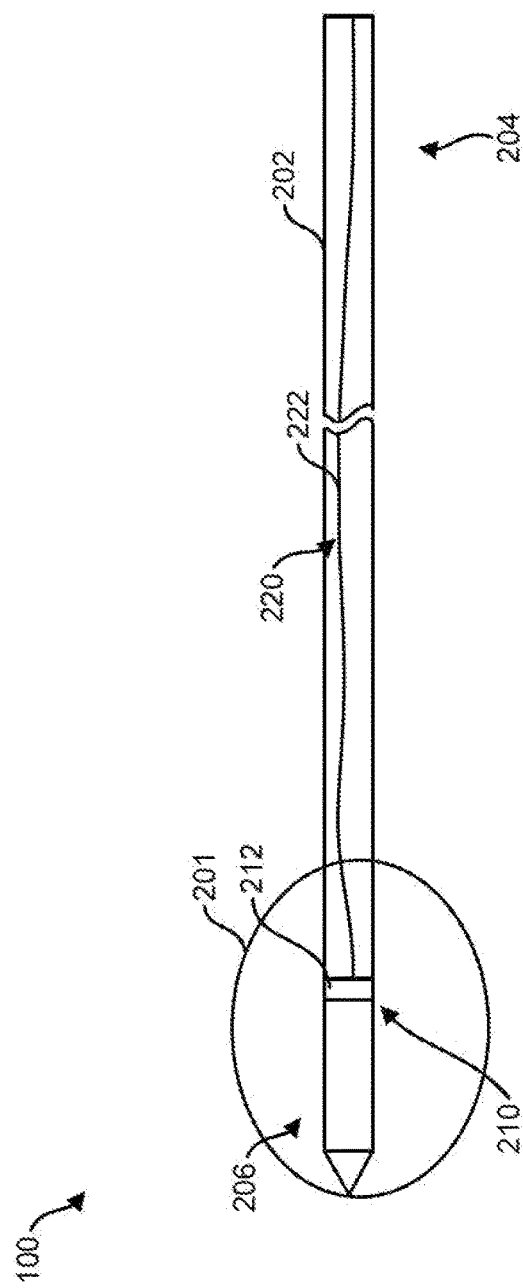
FIG. 2A is an illustration of a cryoablation needle, according to principles of the present disclosure.
Figure 2B:
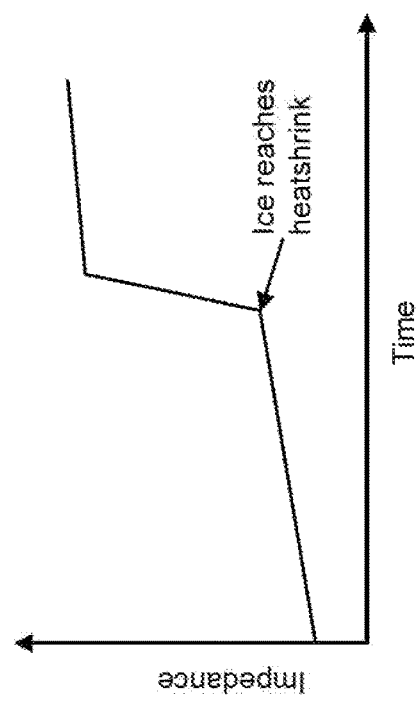
FIG. 2B is a diagram showing a rate of change in impedance over time for the cryoablation needle shown in FIG. 2A.

FIGS. 2A and 2B show various features of an illustrative cryoablation needle 100 according to principles of the present disclosure. FIG. 2A shows a cryoablation needle 100. FIG. 2B shows a diagram of a rate of change in impedance over time for the cryoablation needle 100 shown in FIG. 2A.

As shown in FIG. 2A illustrates, a cryoablation needle 100 can have an iceball 201 formed thereon. The cryoablation needle 100 can include a needle body 202 with a cryoablation needle proximal portion 204 and a cryoablation needle distal portion 206 that is opposite the cryoablation needle proximal portion 204. The cryoablation needle 100 can include an electrode arrangement 210, which can include at least one electrode 212. The electrode arrangement 210 can be disposed at the distal portion of the cryoablation needle 100. The at least one electrode 212 can be configured to generate an impedance (e.g., the at least one electrode can be a sensing electrode). The cryoablation needle 100 can include a conductor wire assembly 220 with at least one conductor wire 222. The conductor wire assembly 212 can be in communication with the electrode arrangement 210, e.g. with the at least one electrode 212. In certain examples, such as when the cryoablation needle 100 includes discrete electrodes 212, a sleeve (e.g., a shrink wrap) can be fitted over the cryoablation needle 100 to fix the electrodes 212 and conductor wires in place for operation. Usefully, in these examples, measures that are indicative of a size or a shape of the iceball 201 can be determined based a rate of change in the impedance (e.g., as shown in FIG. 2B). Several additional features and/or examples of cryoablation needles will be discussed further below, after discussion of methods for using the cryoablation needle 100 in accordance with principles of the present disclosure.

For clarity purposes, it should be understood that the illustrated example is just one of many examples disclosed herein. As such, one skilled in the art would appreciate that many variations of the cryoablation needle 100 may be made without departing from the scope of this invention. For instance, the cryoablation needle 100 is shown with a single electrode 212 and a single conductor wire 222. In certain instances, there can be other sensing elements and conductor wires 222 present and/or more than one wire connected to each electrode. In certain instances, the electrodes can be sensing electrodes, sensors, or any other suitable electromechanical devices or sensing media, none of which is outside the scope of this disclosure.

Figure 3:
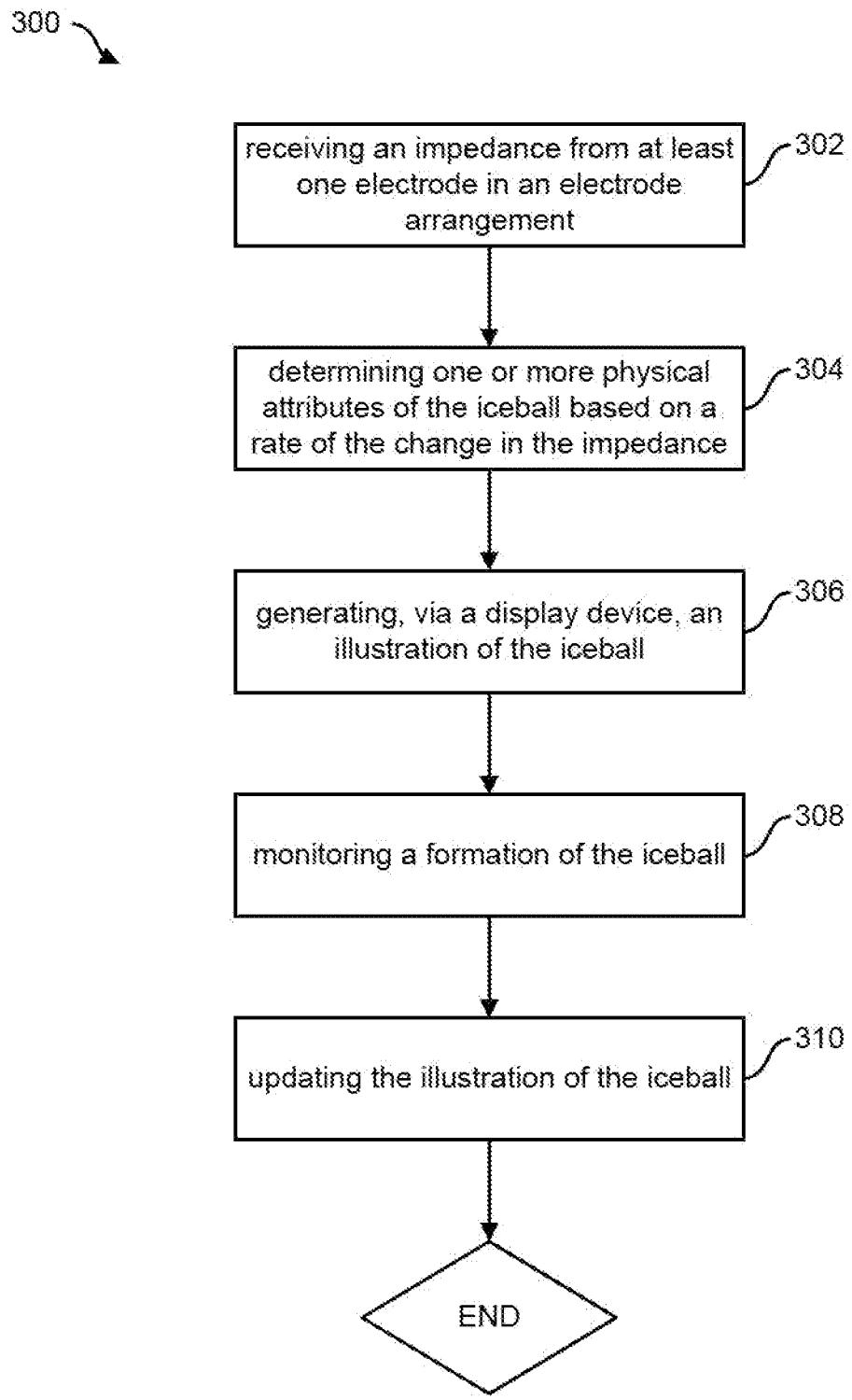
FIG. 3 is a flowchart of a method, according to principles of the present disclosure.

Methods for monitoring a formation of an iceball at a cryoablation needle are disclosed herein. FIG. 3 is a flowchart of a method 300, according to principles of the present disclosure. As discussed herein, methods, including the method 300, can employ any and all features of the cryosurgery system 10 and/or the cryoablation needle 100 discussed above and/or hereinafter.

In the illustrated example, the method 300 can include at step 302 receiving an impedance from at least one electrode in an electrode arrangement that is disposed at a cryoablation needle distal portion. The electrode arrangement can be configured to engage the iceball as the iceball is formed over the cryoablation needle distal portion so as to cause a change in the impedance. In certain instances, where multiple iceballs are formed on respective separate cryoablation needles, the electrode arrangement can be configured to engage multiple iceballs. At step 304, the method 300 can include determining one or more physical attributes of the iceball based on a rate of the change in the impedance. In examples, the one or more physical attributes can include at least one of a size and a shape of the iceball. Further details of principles for determining the one or more physical attributes with be discussed further below.

Principles of the present disclosure can provide a visual display of formation of an iceball. In examples, at step 306, the method 300 can include generating, via a display device, an illustration of an iceball that has the one or more physical attributes that have been determined. For instance, the display device can generate the illustration on a graphic user interface for deciphering by a practitioner. In this regard, in examples, at step 308 the method 300 can include monitoring a formation of the iceball, e.g., as the iceball changes in form over time. In examples, at step 310 the method 300 can include updating the illustration of the iceball when the one or more physical attributes of the iceball changes.

Physical attributes of the iceball can be determined by using varied numbers of reference points positioned at the cryoablation needle. For instance, as previously discussed, the cryoablation needle can include at least one reference location. In examples, the rate of change in the impedance can be based on at least one reference location that defines various distances. In examples, the rate of the change in the impedance can be based on at least one reference location that is positioned along a length of the cryoablation needle. For instance, the at least one reference location can be indicative of a distance from a tip section of a cryoablation needle distal portion to either the first electrode or the second electrode or a distance that corresponds to the distance between the first electrode and the second electrode. In certain instances, the at least one reference location can include a first reference location. The first reference location can be positioned a distance from a tip section of the cryoablation needle distal portion to the at least one electrode. As discussed further below, examples disclosed herein can include more than one reference location (e.g., first, second, and third reference locations and so on).

Figure 4:
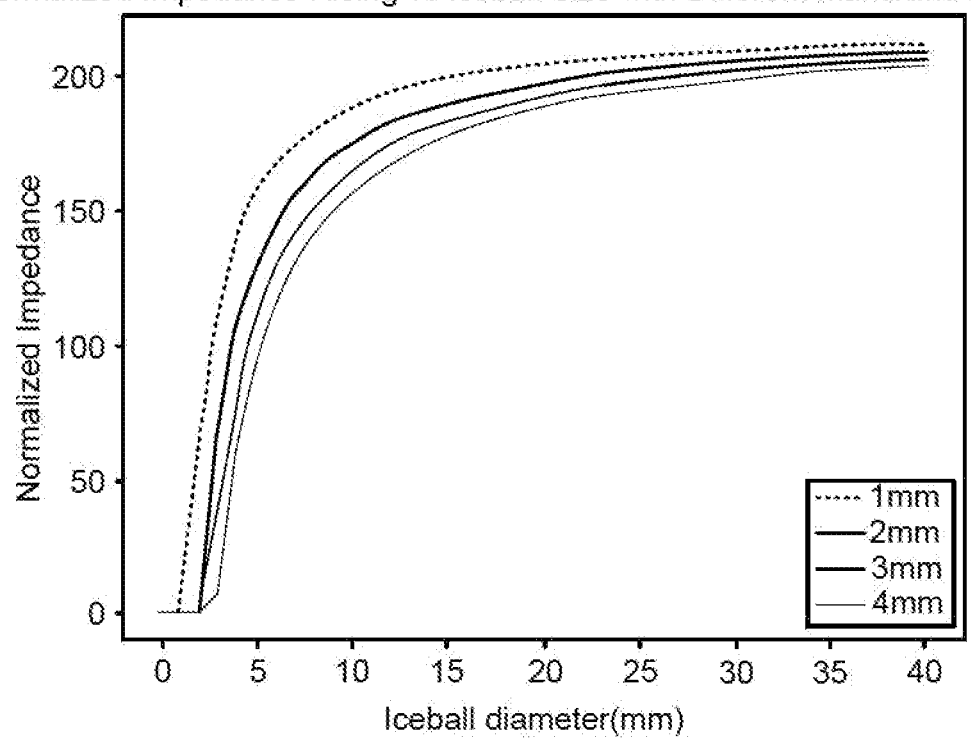
FIG. 4 is a diagram with a rate of change in impedance, according to principles of the present disclosure.

Models such as analytical models may be useful in determining physical attributes of the iceball. FIG. 4 shows a diagram with a rate of change in impedance. In particular, the impedance illustrated here is a normalize impedance and is shown with respect to different electrode lengths (e.g., 1, 2, 3, and 4 mm). The nonlinear nature of the lines in the diagram are indicative of a nonlinear output to a given input. In examples, determining one or more physical attributes of the iceball based on the rate of the change in the impedance can be performed using a model. For instance, the model can include a transfer function, which generally is a representation of a time-dependent correlation between an input and output by using a Laplace transform. In this regard, a transfer function employed in this disclosure can correlate the one or more physical attributes to the rate of the change in the impedance, accommodating for the nonlinear nature of the lines. For example, the transfer function can be a nonlinear transfer function between ice thickness (e.g., over the electrode) and impedance change.

Figure 5:
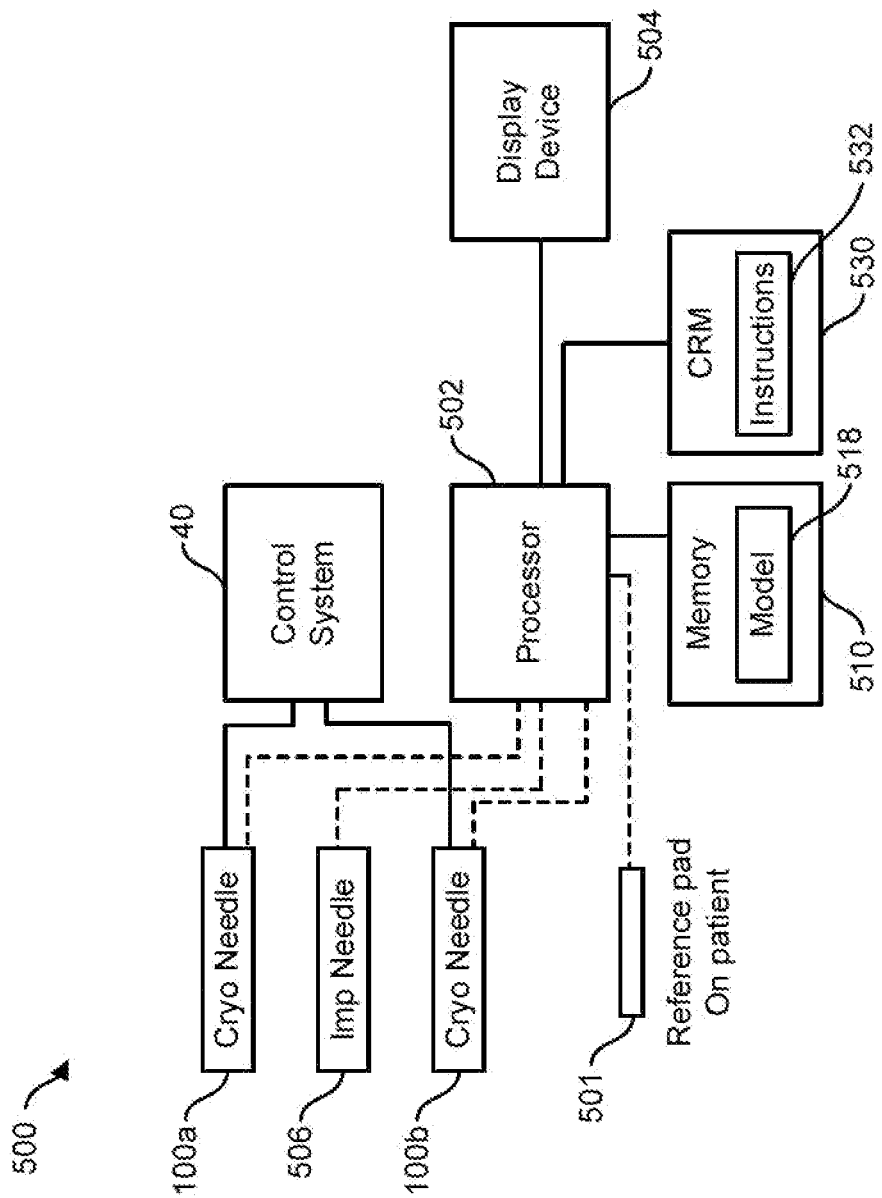
FIG. 5 is a diagram of a data processing system, according to principles of the present disclosure.

FIG. 5 shows various features of a data processing system 500. The data processing system 500 can include any and all features of the cryoablation needles and related systems and methods discussed elsewhere herein, including the cryoablation needle 100, the system 10, and the method 300.

As shown here, the data processing system 500 is configured for visualization and planning with a variety of reference locations. The reference locations can be on a patient (e.g., via a reference pad 501), on a sheath, on an electrode that is disposed at one or more cryoablation needles 100a, 100b, and/or on the one or more cryoablation needles 100a, 100b themselves. Under these circumstances, an imaging method such as MRI, CT, or ultrasound can be used to display an image of one or more cryoablation needles 100a, 100b that is within a patient during operation. As shown, multiple cryoablation needles 100a, 10013 can be employed with a control system 40 and are connected to a processor 502 (e.g., an impedance sensing unit). The processor 502, as discussed elsewhere herein, can employ time switching or multiple frequencies for concurrent impedance sensing. Optionally, and illustrated here, an impedance needle 506 with cryocapability can be placed between or around the one or more cryoablation needles 100a, 100b to sense growth of the iceball. In examples, impedance can be measured between a needle to the reference pad 501, between needle and needle, or between electrodes (e.g., in the form of a segment of the needle shaft or a discrete electrode) on the same needle. As used therein, needle can refer to the one or more cryoablation needles 100a, 100b and/or the impedance needle 506. The display device 504 can display, among other things, a representation of physical attributes (e.g., size, shape, etc.) of the iceball in real time. In examples, the display device 504 can also display any information that contributes to the determination of the physical attributes of the iceball.

Computer-implemented methods and systems that employ such methods are also disclosed herein. For example, the data processing system 500 can include a memory 510 for storing one or more models 518, such as the model discussed in relation to FIG. 4, and any ancillary modules. In addition, or in alternative, the data processing system 500 can include either the processor 502 or a computer 502, each of which can be configured to access the memory 510. In this regard, exemplary procedures in accordance with the present disclosure described herein can be performed by a processing arrangement (e.g., one or more processors 502), a computing arrangement (e.g., one or more computers 502), or both. Such arrangements can be, e.g., entirely or a part of, or include, but not limited to, a computer 502, a processor 502, or both, each of which can include, e.g., one or more processors 502 (e.g., CPUs or microprocessors), and use a non-transitory computer-readable medium ("CRM") 530 (e.g., RAM, ROM, hard drive, or other storage device) with instructions 532 stored thereon. Although depicted here in a certain arrangement, the data processing system 500, as one skilled in the art will appreciate, can perform essentially the same functions in other arrangements (e.g., where the CRM 530, display device 504, and the memory 510 are provided by one component, such as a mobile device or a computer.

In examples of computer-implemented methods, illustrations of the physical attributes of one or more iceballs can be generated for use on the display device 504. As shown here, in examples, multiple cryoablation needles 100a, 100b can be connected to the processor 502. In this regard, determining the one or more physical attributes of one or more iceballs based on the rate of the change in the impedance is performed via a processor 502 that is in communication with an electrode arrangement on each of the multiple cryoablation needles 100a. Under these circumstances, time switching, multiple frequencies, and the like can be employed for concurrent impedance sensing across one or more electrodes on a given cryoablation needle and across the multiple cryoablation needles 100a. The processor 502 can be in communication with the display device 504, which, according to some examples of the present disclosure, can be a touchscreen configured to input information to the processor 502 in addition to outputting information from the processor 502. Further, the display device 504, the memory 518, or both can be used to display, store, or both display and store certain data (e.g., time, impedances, physical attributes of iceballs, etc.) in a format that is either or both user-readable and user-accessible.

Continuing with these examples, as previously discussed, monitoring a formation of the iceball and updating the illustration of the iceball can ensue. In this regard, the processor 502 can be included in an impedance sensing unit. Impedance measurements (e.g., taken by the impedance sensing unit) can be unipolar (electrode to indifferent), bipolar (between two electrodes on the same cryoablation needle, between an electrode on the cryoablation needle (e.g., 100a) and a separate cryoablation needle (e.g., 100b)), or quadripolar impedances can monitor tissue impedance changes without regard to electrode. An adaptive current output can be employed as impedance increases (e.g., such that higher resolution occurs at lower impedance values and lower resolution but higher dynamic range occurs at higher impedance values).

Such computer-implemented methods can include the non-transitory computer-readable medium 530 with processor-executable instructions 532 for reading data from a processor. The processor can be in communication with at least one electrode in an electrode arrangement disposed at a cryoablation needle. When installed on a device, such as a computer, the processor-executable instructions 532 can enable the device to perform actions. Those actions can be similar to, and thus include all the features of, those of the methods disclosed elsewhere herein. For example, the actions can include receiving an impedance from the at least one electrode in the electrode arrangement that is disposed at a cryoablation needle distal portion. The electrode arrangement can be configured to engage an iceball as the iceball is formed over the cryoablation needle distal portion so as to cause a change in the impedance. The actions can include determining one or more physical attributes of the iceball based on at least one of the impedance and a reference location that is positioned at the cryoablation needle. In examples, as discussed elsewhere herein, the one or more physical attributes includes at least one of a size and a shape of the iceball.

In examples, the actions can include generating, via a display device 504, an illustration of an iceball that has the one or more physical attributes that have been determined. For instance, the display device 504 can generate the illustration on a graphic user interface for deciphering by a practitioner. In this regard, in examples, the actions can include monitoring a formation of the iceball, e.g., as the iceball changes in form over time. In examples, the actions can include updating the illustration of the iceball when the one or more physical attributes of the iceball changes. As noted elsewhere herein as it pertains to the method, in examples, determining a physical attribute of the iceball based on at least one of the impedance and the reference location that is positioned at the cryoablation needle can include using a transfer function that correlates the physical attribute to a rate of the change in the impedance.

Figure 6A:
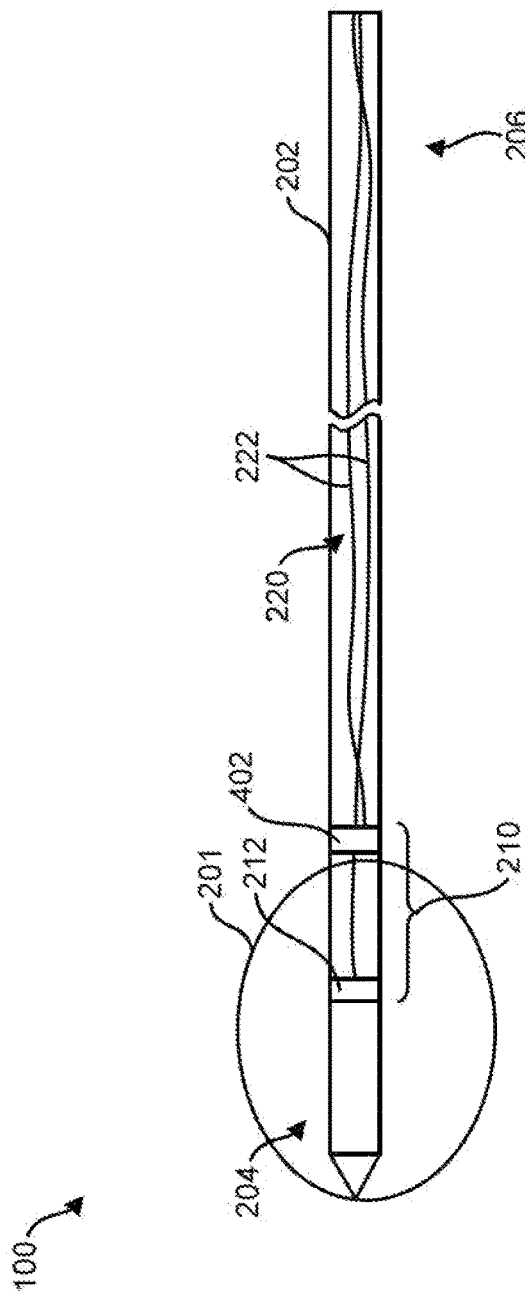
FIG. 6A is an illustration of a cryoablation needle with multiple, discrete electrodes, according to principles of the present disclosure.
Figure 6B:
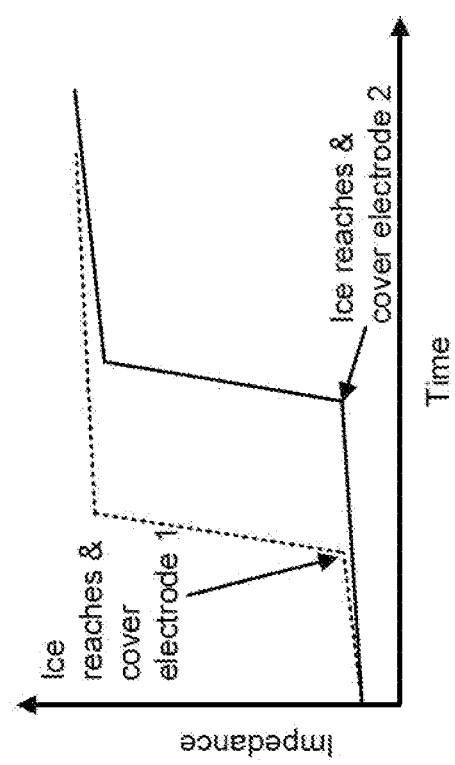
FIG. 6B is a diagram of a rate of change in impedance for the cryoablation needle shown in FIG. 6A.
Figure 7A:
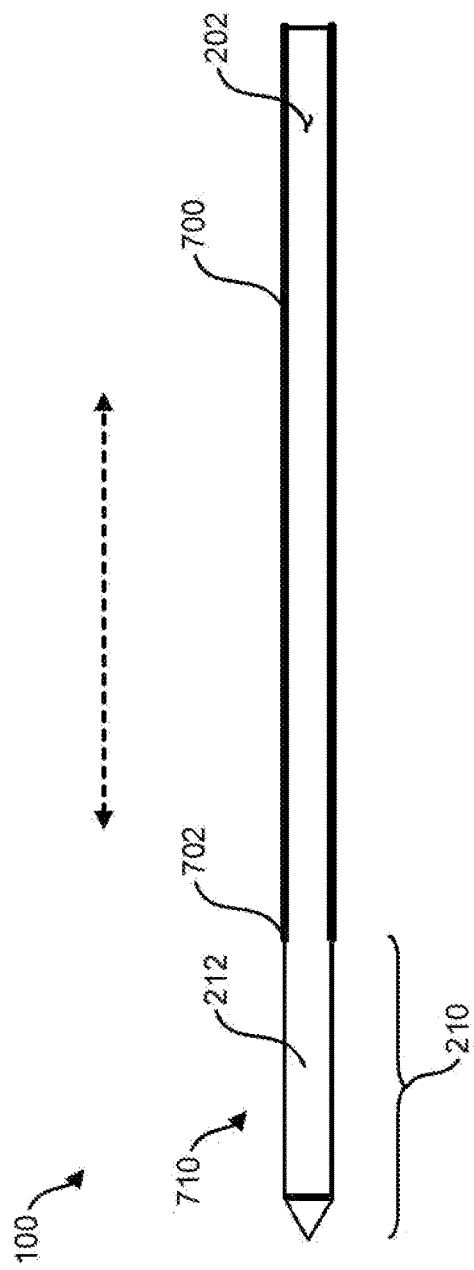
FIG. 7A is an illustration of a sheathed cryoablation needle, according to principles of the present disclosure.
Figure 7B:
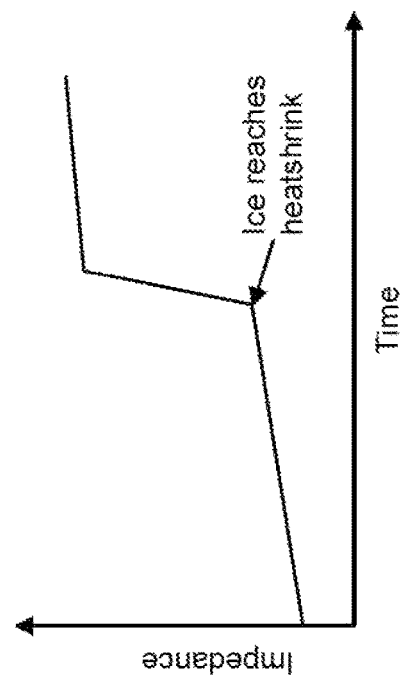
FIG. 7B is a diagram of a rate of change in impedance for the cryoablation needle shown in FIG. 7A.
Figure 8A:
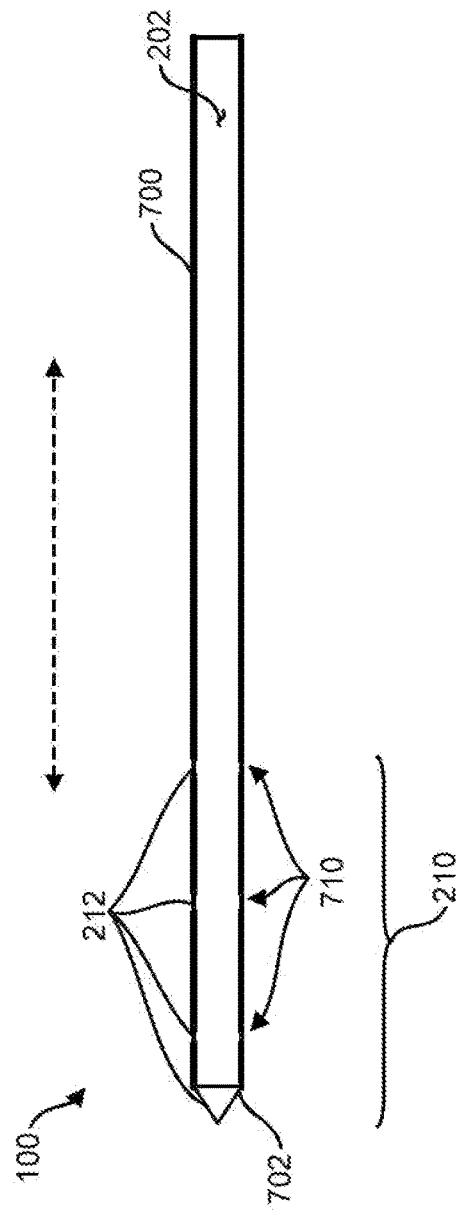
FIG. 8A is an illustration of a sheathed cryoablation needle with multiple sensing locations, according to principles of the present disclosure.
Figure 8B:
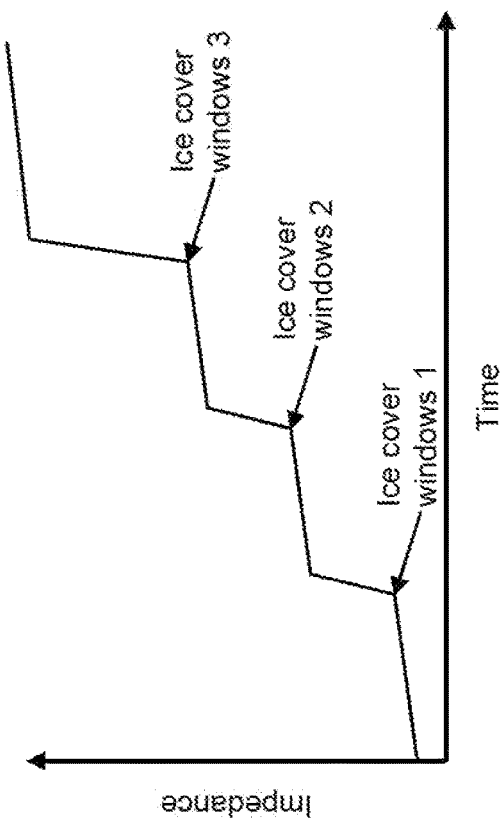
FIG. 8B shows a diagram of a rate of change in impedance for the cryoablation needle shown in FIG. 8A.

Various configurations of the cryoablation needle 100 are shown in FIGS. 6A, 6B, 7A, 7B, 8A, and 8B. In particular, FIGS. 6A and 6B relate to a cryoablation needle 100 that is similar to those discussed in relation to FIGS. 2A and 2B but with multiple, discrete electrodes 212. In particular, FIG. 6A shows the cryoablation needle 100 with multiple, discrete electrodes 212, and FIG. 6B shows a diagram of a rate of change in impedance for the cryoablation needle 100 shown in FIG. 6A. FIGS. 7A and 7B relate to a sheathed cryoablation needle 100 where the cryoablation needle body 202 functions as an electrode 212 such that there is a single, adjustable electrode. In particular, FIG. 7A shows the sheathed cryoablation needle 100, and FIG. 7B shows a diagram of a rate of change in impedance for the cryoablation needle 100 shown in FIG. 7A. FIGS. 8A and 8B relate to a sheathed cryoablation needle 100 where the cryoablation needle body 202 functions as an electrode with multiple, discrete sensing locations 212. In particular, FIG. 8A shows the sheathed cryoablation needle 100 with multiple sensing locations, and FIG. 8B shows a diagram of a rate of change in impedance for the cryoablation needle 100 shown in FIG. 8A. It should be noted that the cryoablation needles in these figures can be similar to and thus include any and all features of those cryoablation needles discussed elsewhere herein. As well, the cryoablation needle 100 can be similarly employed in the devices, systems, and methods discussed elsewhere herein.

With reference to FIG. 6A, the electrode arrangement 210 can include a plurality of electrodes 212. In this regard, the plurality of electrodes 212 can include any number of electrodes 212 (e.g., all even and/or odd numbers such as 1, 2, 5, 9, 12, etc.). For illustration, the example shown here includes two electrodes, a first electrode 212 and a second electrode 402. In this regard, the at least one electrode 212 discussed with respect to FIG. 2A can be a first electrode 212 and the plurality of electrodes 212 can include the first electrode 212 and a second electrode 402. The at least one reference location can define a distance that corresponds to the distance between the first electrode 212 and the second electrode 402. In examples, the second electrode 402 can be disposed at a position that is proximal to the first electrode 212. For example, the first and second electrodes 212 can be arranged longitudinally (e.g., equally or randomly spaced apart or stacked in any combination or arrangement). In all other respects, the second electrode 402 can be configured similarly to the first electrode 212, e.g., such that the processor is in communication with and can sense an impedance from the second electrode 402. With such an arrangement, in a non-limiting example, an expansion of a capacity for the cryoablation needle 100 to determine the size and shape of the iceball can be achieve. In addition, or in alternative, continuing with the size and shape example, an accuracy of determination can be improved at least because the second electrode 402 provides another reference location and impedance measurement for the model. Adding additional electrodes 212 can further improve these capabilities.

A sheathed cryoablation needle 100 is shown in FIGS. 7A, 7B, 8A, and 8B. In examples, the needle body 202 can be received by a sheath 700. In certain examples, the sheathed cryoablation needle 100 can be snugly received by the sheath 700 so as to be relatively fixed with respect to the needle body 202. In other examples, the sheathed cryoablation needle 100 can be movably received by the sheath 700. In this regard, the sheath 700 can be slidable in both the proximal and distal directions (as indicated by the dashed double arrow) relative to the needle body 202.

In examples, the cryoablation needle 100 can include a needle body 202 that is formed of a conducive material and a sheath 700 that is formed of a nonconductive material. For instance, the needle body 202 can comprise a conductive metal such as stainless steel. In certain instances, the needle body 202 can comprise multiple conductive materials, such as having a gold-plated and/or copper tip. The sheath 700 can be an insulative covering such as a PTFE heat shrink or a fluoropolymer coating. In certain examples, the insulative covering can comprise multiple materials such as PTFE, FEP, PFA, PET, PEEK, Polyimide, etc., at a sheath 700 proximal portion and fluoropolymer at a sheath 700 distal portion.

Certain sections of the sheath 700 can cover the needle body 202 with certain sections (e.g., windows 710) removed to facilitate the needle body 202 as impedance sensing electrode. In other words, each window can form a sensing location such that the underlying needle body 202 serves as an electrode 212 at each window 710. As previously discussed, the cryoablation needle 100 can include a needle body 202 that is formed of a conducive material and a sheath 700 that is formed of a nonconductive material. The sheath 700 can have one or more windows 710 formed therein or can comprise a plurality of individual sleeve segments. In this regard, the sheath 700 can form one or more exposed regions of the needle body 202 and one or more unexposed regions of the needle body 202.

With continued reference to the sheathed catheter configuration, as shown in FIG. 7A, the at least one electrode 212 can include a first exposed region of the one or more exposed regions. In this instance, the first exposed region extends from the sheath distal end 702 to the tip of the needle body 202. As the iceball grows over time, windows 710 (e.g., the first exposed region in this instance) can be sequentially (e.g., in a distal-to-proximal direction) covered by the growing iceball. As can be seen in FIG. 7B, impedance can correspondingly rise when iceball covers the sheath 700 and with multiple discrete steps as the iceball grows to cover a corresponding window 710 along the length of the needle body 202. The iceball engaging the sheath 700 can cause the impedance to rise more sharply than when the iceball engages the needle body 202 through windows 710. Such relationships can be used to monitor formation of the iceball.

Under certain circumstances, as can be seen in FIG. 8A, the electrode arrangement 210 can include a plurality of windows 710 such that the needle body 202 can function as an electrode 212 at the sensing location formed at the exposed regions by each window 710. In other words, the at least one electrode 212 can include an electrode arrangement 210 that functions as a plurality of electrodes 212 by way of the sensing locations formed between the windows 710 in the sheath 700 and the needle body 202. For example, the one or more exposed regions can include a plurality of exposed regions. In this regard, each of the electrodes 212 in the plurality of electrodes 212 corresponds to an exposed region within the plurality of exposed regions. The at least one electrode 212 can include a first exposed region of the one or more exposed regions. The at least one electrode 212 can include a second exposed region of the one or more exposed regions. Continuing in this manner, an increasing number of electrodes 212 (e.g., 3, 5, 8, 11, etc.) can correspond to an increasing number of exposed regions. In examples, the at least one electrode 212 comprises a plurality of electrodes 212 and the one or more exposed regions include a plurality of exposed regions such that each of the electrodes 212 in the plurality of electrodes 212 corresponds to an exposed region within the plurality of exposed regions. Staggered exposed regions (e.g., when the sheath 700 includes intermediate windows 710 or discrete, spaced apart segments) can monitor iceball formation as the iceball grows/enlarges and/or coalesces with other iceballs. Similar to FIG. 7B, as can be seen in FIG. 8B, impedance can correspondingly rise when iceball covers the sheath 700 and with multiple discrete steps as the iceball grows to cover increasing numbers of corresponding windows 710 along the length of the needle body 202. The iceball engaging the sheath 700 can cause the impedance to rise more sharply than when the iceball engages the needle body 202 through windows 710. Such relationships can be used to monitor formation of the iceball.

With reference to FIGS. 7A and 8A, being movable relative to the needle body 202, the sheath 700 can be moved along a length of the needle body 202. In this manner, movement of the sheath 700 can, for instance, influence formation of the iceball and/or impedance measurements. In the illustrated examples, a sheath distal end 702 is shown proximal to the tip region of the cryoablation needle 100. In an example, from the illustrated position, the sheath distal end 702 can move distally toward the tip region to even cover the tip region. In an example, from the illustrated position, the sheath distal end 702 can move proximally away from the tip region to reveal more of the needle body 202. As was previously discussed, when the needle body 202 comprises a conductive material, the exposed region (e.g., the region not covered by the sheath 700) can be an electrode for use in the aforementioned methods. Under certain circumstances, for example when the sheath 700 can be moved both proximally and distally, the electrode can be said to be an adjustable length electrode. In this regard, the length of the electrode can influence the physical attributes (e.g., size, shape, etc.) of the iceball. For instance, in some circumstances, the exposed region can facilitate formation of an iceball thereon, and the unexposed region (e.g., those covered by the sheath 700) can inhibit formation of the iceball thereon.

The sheath 700 can be integrally or separately formed. In some embodiments, the sheath 700 comprises discrete sheath 700 segments such that the exposed region in a window 710 between any two given sheath 700 segments is adjustable. In some embodiments, the windows 710 are a fixed distance apart as the sheath 700 moves along the length of the needle body 202. Other embodiments can have some combination of adjustable and fixed windows 710.

Measured impedances can be useful in other manners that fall well within the scope of the present disclosure. In examples, the actions can include determining whether one or more iceballs have coalesced (e.g., two iceballs coalescing into one iceball) because there will be a corresponding change in impedance. Measured impedances can facilitate monitoring when the cryoablation needle 100 is in tissue versus air or in different types of tissue. Measured impedances can facilitate monitoring changes around the electrodes 212 before and after cryoablation. Determined physical attributes of the iceball can be used as feedback to a processor as it controls a flow of cryogas to optimize the cryogas consumption. For example, after the iceball reaches a certain size, less cryogas (such as argon) is needed to maintain it. In this regard, the processor can cause the flow of cryogas to decrease. Of course, there may be instances where the processor can cause the flow of cryogas to increase, as will be appreciated by one skilled in the art.

It is well understood that methods that include one or more steps, the order listed is not a limitation of the claim unless there are explicit or implicit statements to the contrary in the specification or claim itself. It is also well settled that the illustrated methods are just some examples of many examples disclosed, and certain steps can be added or omitted without departing from the scope of this disclosure. Such steps can include incorporating devices, systems, or methods or components thereof as well as what is well understood, routine, and conventional in the art.

The connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements. The scope is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B or C may be present in a single embodiment; for example, A and B, A and C, B and C, or A and B and C.

In the detailed description herein, references to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art with the benefit of the present disclosure to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element herein is to be construed under the provisions of 35 U.S.C. 112(f), unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A method for monitoring a formation of an iceball at a cryoablation needle, the method comprising:
receiving an impedance from at least one electrode in an electrode arrangement that is disposed at a cryoablation needle distal portion, the electrode arrangement is configured to engage the iceball as the iceball is formed over the cryoablation needle distal portion so as to cause a change in the impedance; and
determining one or more physical attributes of the iceball based on a rate of the change in the impedance.

2. The method of claim 1, wherein the one or more physical attributes includes at least one of a size and a shape of the iceball.

3. The method of claim 2, wherein the rate of the change in the impedance is based on at least one reference location that is positioned at the cryoablation needle.

4. The method of claim 3, wherein the at least one reference location includes a first reference location that is a distance from a tip section of the cryoablation needle distal portion to the at least one electrode.

5. The method of claim 3, wherein the electrode arrangement comprises a plurality of electrodes such that the at least one electrode is a first electrode and such that the plurality of electrodes includes the first electrode and a second electrode, and wherein the at least one reference location comprises a value that is indicative of a distance between the first electrode and the second electrode.

6. The method of claim 5, wherein the second electrode is disposed at a position that is proximal to the first electrode.

7. The method of claim 1, wherein the cryoablation needle comprises a needle body that is formed of a conducive material and a sheath that is configured to receive the needle body so as to form one or more exposed regions of the needle body and one or more unexposed regions of the needle body, wherein the at least one electrode comprises a first exposed region of the one or more exposed regions.

8. The method of claim 7, wherein the at least one electrode comprises a plurality of electrodes and the one or more exposed regions comprises a plurality of exposed regions such that each of the electrodes in the plurality of electrodes corresponds to an exposed region within the plurality of exposed regions.

9. The method of claim 7, wherein the needle body is movably received with the sheath.

10. The method of claim 1, wherein determining one or more physical attributes of the iceball based on the rate of the change in the impedance comprises using a transfer function that correlates the one or more physical attributes to the rate of the change in the impedance.

11. The method of claim 10, wherein determining the one or more physical attributes of the iceball based on the rate of the change in the impedance is performed via a processor that is in communication with the electrode arrangement.

12. A non-transitory computer-readable medium having processor-executable instructions for reading data from a processor in communication with at least one electrode in an electrode arrangement disposed at a cryoablation needle, the processor-executable instructions when installed on a device enable the device to perform actions, comprising:
receiving an impedance from the at least one electrode in the electrode arrangement that is disposed at a cryoablation needle distal portion, the electrode arrangement is configured to engage an iceball as the iceball is formed over the cryoablation needle distal portion so as to cause a change in the impedance; and
determining one or more physical attributes of the iceball based on at least one of the impedance and a reference location that is positioned at the cryoablation needle.

13. The non-transitory computer-readable medium of claim 12, wherein the one or more physical attributes includes at least one of a size and a shape of the iceball.

14. The non-transitory computer-readable medium of claim 12, wherein the actions further comprise:
generating, via a display device, an illustration of an iceball that has the one or more physical attributes that have been determined;
monitoring a formation of the iceball; and
updating the illustration of the iceball when the one or more physical attributes of the iceball changes.

15. The non-transitory computer-readable medium of claim 12, wherein determining a physical attribute of the iceball based on at least one of the impedance and the reference location that is positioned at the cryoablation needle comprises using a transfer function that correlates the physical attribute to a rate of the change in the impedance.

16. The non-transitory computer-readable medium of claim 12, wherein the actions further comprise determining whether one or more iceballs have coalesced.

17. A cryoablation needle comprising:
a needle body that has a proximal portion and a distal portion that is opposite the proximal portion;
an electrode arrangement that includes at least one electrode; the electrode arrangement disposed at the distal portion of the cryoablation needle, the at least one electrode configured to generate an impedance; and
a conductor wire assembly that includes at least one conductor wire, the conductor wire assembly is in communication with the electrode arrangement such that measures that are indicative of a size or a shape of the iceball can be determined based a rate of change in the impedance.

18. The cryoablation needle of claim 17, wherein the cryoablation needle comprises a needle body that is formed of a conducive material and a sheath that is configured to receive the needle body so as to form one or more exposed regions of the needle body and one or more unexposed regions of the needle body, wherein the at least one electrode comprises a first exposed region of the one or more exposed regions, and wherein the at least one electrode comprises a plurality of electrodes and the one or more exposed regions comprises a plurality of exposed regions such that each of the electrodes in the plurality of electrodes corresponds to an exposed region within the plurality of exposed regions.

19. The cryoablation needle of claim 18, wherein the needle body is movably received with the sheath.

20. The cryoablation needle of claim 17,
wherein the electrode arrangement comprises a plurality of electrodes such that the at least one electrode is a first electrode and such that the plurality of electrodes includes the first electrode and a second electrode; and
wherein the rate of change in the impedance is based on at least one reference location that is indicative of a distance from a tip section of a cryoablation needle distal portion to either the first electrode or the second electrode or a distance that corresponds to the distance between the first electrode and the second electrode.

* * * * *